US012769813B2

(12) United States Patent
Aoki et al.

(10) Patent No.: US 12,769,813 B2
(45) Date of Patent: Oct. 20, 2026

(54) INFORMATION PROCESSING SYSTEM, INFORMATION PROCESSING METHOD, AND RECORDING MEDIUM

(71) Applicant: NEC Corporation, Minato-ku (JP)

(72) Inventors: Noriyuki Aoki, Tokyo (JP); Hiroaki Suzuki, Tokyo (JP); Fengqian Lou, Tokyo (JP); Yuki Shimizu, Tokyo (JP); Hirokazu Akiba, Tokyo (JP); Yusuke Usui, Tokyo (JP)

(73) Assignee: NEC CORPORATION, Tokyo (JP)

( * ) Notice: Subject to any disclaimer, the term of this patent is extended or adjusted under 35 U.S.C. 154(b) by 199 days.

(21) Appl. No.: 18/569,257

(22) PCT Filed: Jun. 14, 2021

(86) PCT No.: PCT/JP2021/022509

§ 371 (c)(1),
(2) Date: Dec. 12, 2023

(87) PCT Pub. No.: WO2022/264206

PCT Pub. Date: Dec. 22, 2022

(65) Prior Publication Data

US 2024/0354386 A1 Oct. 24, 2024

(51) Int. Cl.
*G06F 21/32* (2013.01)
*G16H 50/30* (2018.01)

(52) U.S. Cl.
CPC ............. *G06F 21/32* (2013.01); *G16H 50/30* (2018.01)

(58) Field of Classification Search
CPC .......... G06F 21/30; G06F 21/31; G06F 21/32; G16H 15/00; G16H 50/30
See application file for complete search history.

(56) References Cited

U.S. PATENT DOCUMENTS

2018/0197624 A1 7/2018 Robaina et al.
2018/0341760 A1* 11/2018 Frempong ............ H04W 12/63
(Continued)

FOREIGN PATENT DOCUMENTS

CN 111564224 A 8/2020
CN 111951444 A 11/2020
(Continued)

OTHER PUBLICATIONS

JP Office Action for JP Application No. 2023-529166, mailed on Dec. 3, 2024 with English Translation.
(Continued)

*Primary Examiner* — Boris D Grijalva Lobos
(74) *Attorney, Agent, or Firm* — Sughrue Mion, PLLC

(57) ABSTRACT

An information processing system includes: an authentication unit that performs biometric authentication by using biometric information about a first user; an acquisition unit that acquires information about an action history of the first user in the case where the biometric authentication is successful; an storage unit that stores the information about the action history; a generation unit that generates risk information indicating a risk related to the first user, on the basis of the stored information about the action history; and an output unit that outputs the risk information about the first user in response to a request of a second user who is different from the first user. According to such an information processing system, it is possible to properly output information indicating a risk related to the user in response to a request.

9 Claims, 19 Drawing Sheets

(56) References Cited

U.S. PATENT DOCUMENTS

| | | | | |
|---|---|---|---|---|
| 2021/0383099 | A1* | 12/2021 | Oberholzer | G06K 7/1417 |
| 2023/0206688 | A1* | 6/2023 | Kagaya | G06V 40/168<br>382/118 |
| 2024/0354386 | A1* | 10/2024 | Aoki | G16H 50/30 |

FOREIGN PATENT DOCUMENTS

| | | | | |
|---|---|---|---|---|
| CN | 111369721 | B | 2/2021 | |
| JP | 2004-065363 | A | 3/2004 | |
| JP | 2011-070248 | A | 4/2011 | |
| JP | 2018-181006 | A | 11/2018 | |
| JP | 2019-159985 | A | 9/2019 | |
| JP | 2020-505675 | A | 2/2020 | |
| JP | 6865321 | B1 | 4/2021 | |
| KR | 101490016 | B1 * | 2/2015 | G06V 20/52 |
| WO | 2011/055628 | A1 | 5/2011 | |

OTHER PUBLICATIONS

International Search Report for PCT Application No. PCT/JP2021/022509, mailed on Jul. 20, 2021.

* cited by examiner

| ACTION HISTORY INFORMATION | |
|---|---|
| MOVEMENT HISTORY | POSITION INFORMATION, TIME INFORMATION, etc. |
| ENVIRONMENT INFORMATION | AIR TEMPERATURE, AIR PRESSURE, VENTILATION CONDITIONS, etc. |
| HUMAN BODY INFORMATION | BODY TEMPERATURE, PULSE, etc. |
| CONVERSATION HISTORY | CONVERSATION TIME, CONVERSATION TARGET, PRESENCE/ABSENCE OF MASK, etc. |

FIG. 7

INFORMATION PROCESSING SYSTEM, INFORMATION PROCESSING METHOD, AND RECORDING MEDIUM

This application is a National Stage Entry of PCT/JP2021/022509 filed on Jun. 14, 2021, the contents of all of which are incorporated herein by reference, in their entirety.

TECHNICAL FIELD

This disclosure relates to technical fields of an information processing system, an information processing method, and a recording medium.

BACKGROUND ART

A known system of this type collects an action history of a user. For example, Patent Literature 1 discloses a technology/technique of observing the action and behavior of the user by using a nameplate type sensor node, and collecting acquired data by using wireless communication. Patent Literature 2 discloses a technology/technique of detecting entry/exit of the user by using a portable terminal, and storing log data associated with an entry/exit history. Patent Literature 3 discloses a technology/technique of collecting the action history of an infected patient, and preparing an action list and mapping on a map.

As another related technique/technology, Patent Literature 4 discloses a technology/technique of authenticating the user by using a wearable terminal. Patent Literature 5 discloses a technology/technique of attaching a sensor to a headphone and identifying a user from a difference in acoustic characteristics of ears and features of a body.

CITATION LIST

Patent Literature

Patent Literature 1: International Publication No. WO2011/055628

Patent Literature 2: JP2018-181006A

Patent Literature 3: JP2011-070248A

Patent Literature 4: JP2020-505675A

Patent Literature 5: JP2004-065363A

SUMMARY

Technical Problem

This disclosure aims to improve the techniques/technologies disclosed in Citation List.

Solution to Problem

An information processing system according to an example aspect of this disclosure includes: an authentication unit that performs biometric authentication by using biometric information about a first user; an acquisition unit that acquires information about an action history of the first user in the case where the biometric authentication is successful; an storage unit that stores the information about the action history; a generation unit that generates risk information indicating a risk related to the first user, on the basis of the stored information about the action history; and an output unit that outputs the risk information about the first user in response to a request of a second user who is different from the first user.

An information processing method according to an example aspect of this disclosure is an information processing method executed by at least one computer, the information processing method including: performing biometric authentication by using biometric information about a first user; acquiring information about an action history of the first user in the case where the biometric authentication is successful; storing the information about the action history; generating risk information indicating a risk related to the first user, on the basis of the stored information about the action history; and outputting the risk information about the first user in response to a request of a second user who is different from the first user.

A recording medium according to an example aspect of this disclosure is a recording medium on which a computer program that allows at least one computer to execute an information processing method is recorded, the information processing method including: performing biometric authentication by using biometric information about a first user; acquiring information about an action history of the first user in the case where the biometric authentication is successful; storing the information about the action history; generating risk information indicating a risk related to the first user, on the basis of the stored information about the action history; and outputting the risk information about the first user in response to a request of a second user who is different from the first user.

BRIEF DESCRIPTION OF DRAWINGS

FIG. 7 is a table illustrating an example of action history information handled by an information processing system according to a third example embodiment handles.

DESCRIPTION OF EXAMPLE EMBODIMENTS

Hereinafter, an information processing system, an information processing method, and a recording medium according to example embodiments will be described with reference to the drawings.

First Example Embodiment

The information processing system according to the first example embodiment will be described with reference to FIG. 1 to FIG. 4.

Hardware Configuration

Figure 1:
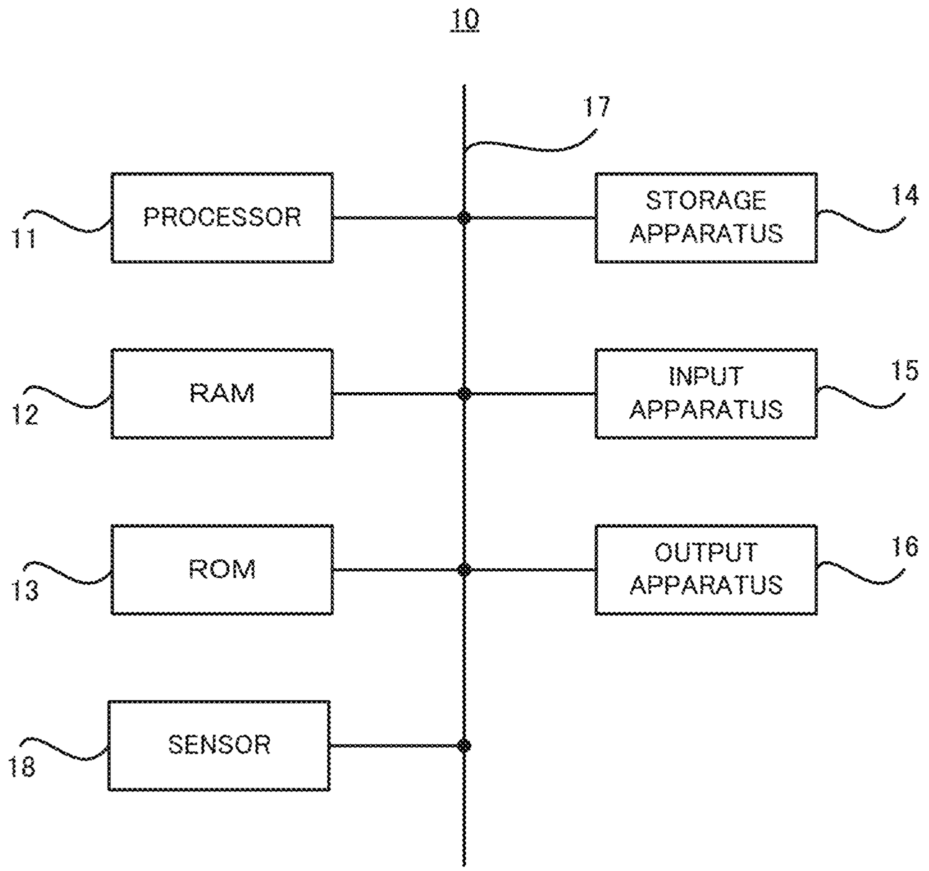
FIG. 1 is a block diagram illustrating a hardware configuration of an information processing system according to a first example embodiment.

First, a hardware configuration of the information processing system according to the first example embodiment will be described with reference to FIG. 1. FIG. 1 is a block diagram illustrating the hardware configuration of the information processing system according to the first example embodiment.

As illustrated in FIG. 1, an information processing system 10 according to the first example embodiment includes a processor 11, a RAM (Random Access Memory) 12, a ROM (Read Only Memory) 13, and a storage apparatus 14. The information processing system 10 may further include an input apparatus 15 and an output apparatus 16. Further, the information processing system 10 includes a sensor 18. The processor 11, the RAM 12, the ROM 13, the storage apparatus 14, the input apparatus 15, and the output apparatus 16, and the sensor 18 are connected through a data bus 17.

The processor 11 reads a computer program. For example, the processor 11 is configured to read a computer program stored by at least one of the RAM 12, the ROM 13 and the storage apparatus 14. Alternatively, the processor 11 may read a computer program stored in a computer-readable recording medium by using a not-illustrated recording medium reading apparatus. The processor 11 may acquire (i.e., may read) a computer program from a not-illustrated apparatus disposed outside the information processing system 10, through a network interface. The processor 11 controls he RAM 12, the storage apparatus 14, the input apparatus 15, and the output apparatus 16 by executing the read computer program. Especially in this example embodiment, in the case where the computer program read by the processor 11 is executed, a functional block for outputting risk information is realized or implemented in the processor 11.

The processor 11 may be configured as, for example, a CPU (Central Processing Unit), a GPU (Graphics Processing Unit), a FPGA (field-programmable gate array), a DSP (Demand-Side Platform) or an ASIC (Application Specific Integrated Circuit). The processor 11 may be one of them, or may use a plurality of them in parallel.

The RAM 12 temporarily stores the computer program to be executed by the processor 11. The RAM 12 temporarily stores the data that are temporarily used by the processor 11 in the case where the processor 11 executes the computer program. The RAM 12 may be, for example, a D-RAM (Dynamic RAM).

The ROM 13 stores the computer program to be executed by the processor 11. The ROM 13 may otherwise store fixed data. The ROM 13 may be, for example, a P-ROM (Programmable ROM).

The storage apparatus 14 stores the data that are stored for a long term by the information processing system 10. The storage apparatus 14 may operate as a temporary storage apparatus of the processor 11. The storage apparatus 14 may include, for example, at least one of a hard disk apparatus, a magneto-optical disk apparatus, a SSD (Solid State Drive), and a disk array apparatus.

The input apparatus 15 is an apparatus that receives an input instruction from a user of the information processing system 10. The input apparatus 15 may include, for example, at least one of a keyboard, a mouse, and a touch panel.

The output apparatus 16 is an apparatus that outputs information about the information processing system 10 to the outside. For example, the output apparatus 16 may be a display apparatus (e.g., a display) that is configured to display the information about the information processing system 10. The output apparatus 16 may be a speaker or the like that is configured to audio-output the information about the information processing system 10. The output apparatus 16 may be configured as a portable terminal such as a smartphone or a tablet.

The sensor 18 is configured to detect information about the user, information about an environment around the user, or the like. The sensor 18 may include a camera (i.e., an image sensor). The sensor 18 may be provided in a wearable terminal. A plurality of sensors 18 or a plurality of types of sensors 18 may be provided. In particular, the sensor 18 according to this example embodiment may be configured to acquire information about an action history described later. The information about the action history will be described in detail later.

Functional Configuration

Figure 2:
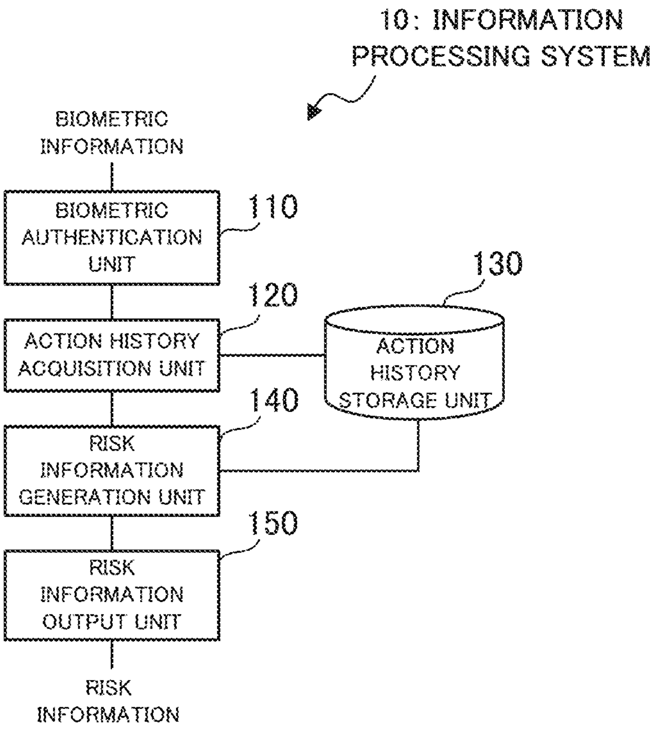
FIG. 2 is a block diagram illustrating a functional configuration of the information processing system according to the first example embodiment.

Next, a functional configuration of the information processing system 10 according to the first example embodiment will be described with reference to FIG. 2. FIG. 2 is a block diagram illustrating the functional configuration of the information processing system according to the first example embodiment.

As illustrated in FIG. 2, the information processing system 10 according to the first example embodiment includes, as components for realizing the functions thereof, a biometric authentication unit 110, an action history acquisition unit 120, an action history storage unit 130, a risk information generation unit 140, and a risk information output unit 150. Each of the biometric authentication unit 110, the action history acquisition unit 120, the risk information generation unit 140, and the risk information output unit 150 may be a processing block that is realized or implemented by the processor 11 (see FIG. 1), for example. The action history storage unit 130 may be realized or implemented by the storage apparatus 14 (see FIG. 1), for example.

The biometric authentication unit 110 is configured to perform biometric authentication by using biometric information about a first user. The biometric authentication unit 110 may be configured to acquire the biometric information about the first user, by using the sensor 18 or the like, for example. In the biometric authentication performed by the biometric authentication unit 110, for example, it may be determined whether or not the first user is a user registered in advance. An aspect of the biometric authentication is not particularly limited, but may be, for example, facial authentication, iris authentication, fingerprint authentication, or the like. A detailed description of a specific technique/technology of the biometric authentication will be omitted here, because the existing techniques/technologies may be adopted as appropriate. An authentication result of the biometric authentication unit 110 is outputted to the action history acquisition unit 120.

The action history acquisition unit 120 is configured to acquire information about an action history of the first user in the case where the biometric authentication of the biometric authentication unit 110 is successful. The action history acquisition unit 120 may acquire the action history by using the sensor 18 or the like, for example. Here, the "information about the action history" is information acquired on the basis of the action history of the user, and may include information about an action and a state of the user, as well as the information about the environment around the user, or the like. Furthermore, the information about the action history may include a plurality of types of information. In the following, for convenience of description, the information about the action history may be referred to as "action history information" as appropriate. A specific example of the action history information will be described in another example embodiment later. The action history information acquired by the action history acquisition unit 120 is configured to be outputted to the action history storage unit 130.

The action history storage unit 130 is configured to store the action history information about the first user acquired by the action history acquisition unit 120. The action history storage unit 130 may be configured to store all the pieces of past action history information about the first use, or may be configured to store only a part of them. The action history storage unit 130 may have a function of deleting the past action history information that is unnecessary, as appropriate. The action history storage unit 130 may be configured as a database managed by a trusted information manager/administrator (e.g., an information bank, a private enterprise designated by a country or a public organization), for example. The action history information stored in the action history storage unit 130 is configured to be read by the risk information generation unit 140.

The risk information generation unit 140 is configured to generate the risk information on the basis of the action history information about the first user stored in the action history storage unit 130. The "risk information" here is information indicating a risk related to the first user. The risk information may be, for example, information including a value indicating a degree of the risk, or may be information indicating the presence or absence of the risk. Although the type of the risk is not particularly limited, an example may be a risk of being infected with an infectious disease. The risk information generated by the risk information generation unit 140 is configured to be outputted to the risk information output unit 150.

The risk information output unit 150 is configured to output the information generated by the risk information generation unit 140. For example, the risk information output unit 150 may be configured to output the risk information by using the output apparatus 16 described above. More specifically, the risk information output unit 150 may be configured to display the risk information on a display, or to audio-output the risk information with a speaker. Furthermore, the risk information output unit 150 is especially configured to output the risk information in response to a request of a second user who is different from the first user (i.e., a user who is different from the user for which the risk information is generated). Examples of the first user and the second user may be a driver of public transportation and passengers thereof, or the like.

Storage Operation

Figure 3:
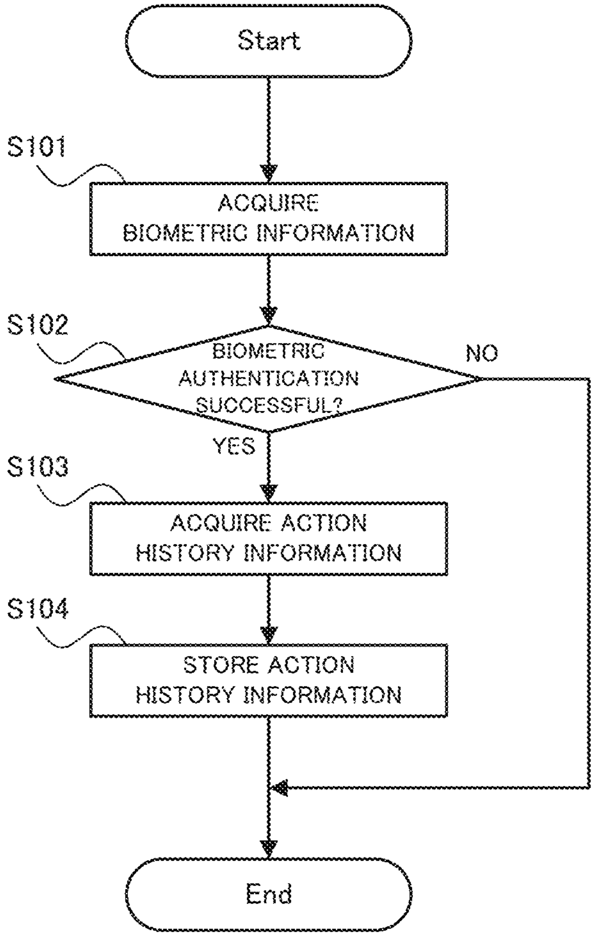
FIG. 3 is a flowchart illustrating a flow of an storage operation of the information processing system according to the first example embodiment.

Next, with reference to FIG. 3, a flow of an operation in the case where the action history information is stored (hereinafter referred to as an "storage operation") by the information processing system 10 according to the first example embodiment will be described. FIG. 3 is a flowchart illustrating the flow of the storage operation of the information processing system according to the first example embodiment.

As illustrated in FIG. 3, in the storage operation by the information processing system 10 according to the first example embodiment, first, the biometric authentication unit 110 acquires the biometric information about the first user (step S101). Then, the biometric authentication unit 110 performs the biometric authentication by using the acquired biometric information about the first user (step S102). In the case where the biometric authentication is failed (step S102: NO), the subsequent processing steps are omitted, and a series of the storage operations is ended (in this case, the biometric information is not stored).

On the other hand, in the case where the biometric authentication is successful (step S102: YES), the action history acquisition unit 120 acquires the action history information about the first user (step S103). Then, the action history storage unit 130 stores the acquired action history information about the first user (step S104).

Output Operation

Figure 4:
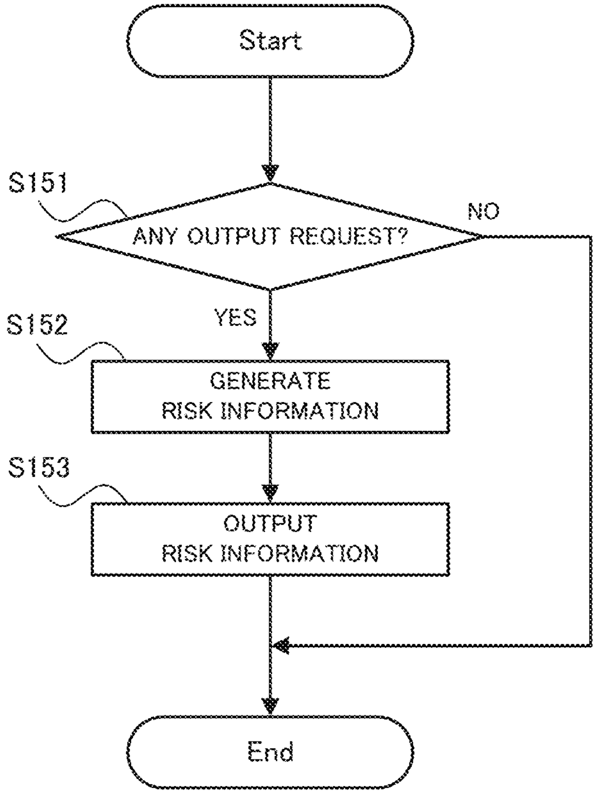
FIG. 4 is a flowchart illustrating a flow of an output operation of the information processing system according to the first example embodiment.

Next, a flow of an operation in the case where the risk information is outputted (hereinafter referred to as an "output operation") by the information processing system 10 according to the first example embodiment will be described with reference to FIG. 4. FIG. 4 is a flowchart illustrating a flow of the output operation of the information processing system according to the first example embodiment.

As illustrated in FIG. 4, in the output operation by the information processing system 10 according to the first example embodiment, first, it is determined whether or not there is an output request from the second user to output the risk information about the first user (step S151). In the case where there is no output request from the second user (step S151: NO), the subsequent processing steps are omitted, and a series of the output operation is ended (in this case, the risk information is not outputted).

On the other hand, in the case where there is an output request from the second user (step S151: YES), the risk information generation unit 140 reads the action history information about the first user stored in the action history storage unit 130, and generates the risk information about the first user (step S152). Then, the risk information output unit 150 outputs the risk information about the first user (step S153).

The risk information output unit 150 typically outputs the risk information to the second user, but the risk information may also be outputted to the first user. Alternatively, the first user may be notified that the risk information is outputted to the second user.

In the above example, the risk information is generated after the output request is made by the second user, but the risk information may be generated before the output request is made by the second user (e.g., in the case where the action history information about the first user is sufficiently stored). In this case, the action history storage unit 130 may be configured to store the generated risk information in addition to the action history information.

Technical Effect

Next, a technical effect acquired by the information processing system 10 according to the first example embodiment will be described.

As described in FIG. 1 to FIG. 4, in the information processing system 10 according to the first example embodiment, the action history information is stored in accordance with the result of the biometric authentication of the first user, and the risk information generated from the action history information is outputted in response to the request from the second user. In this way, it is possible to generate accurate risk information on the basis of the action history information about the first user. Therefore, the second user may be able to accurately understand the risk related to the first user.

Second Example Embodiment

The information processing system 10 according to a second example embodiment will be described with reference to FIG. 5 and FIG. 6. The second example embodiment is partially different from the first example embodiment only in the configuration and operation, and may be the same as the first example embodiment in the other parts. For this reason, a part that is different from the first example embodiment described above will be described in detail below, and a description of other overlapping parts will be omitted as appropriate.

Functional Configuration

First, a functional configuration of the information processing system 10 according to the second example embodiment will be described with reference to FIG. 5. FIG. 5 is a block diagram illustrating the functional configuration of the information processing system according to the second example embodiment. In FIG. 5, the same components as those illustrated in FIG. 2 carry the same reference numerals.

Figure 5:
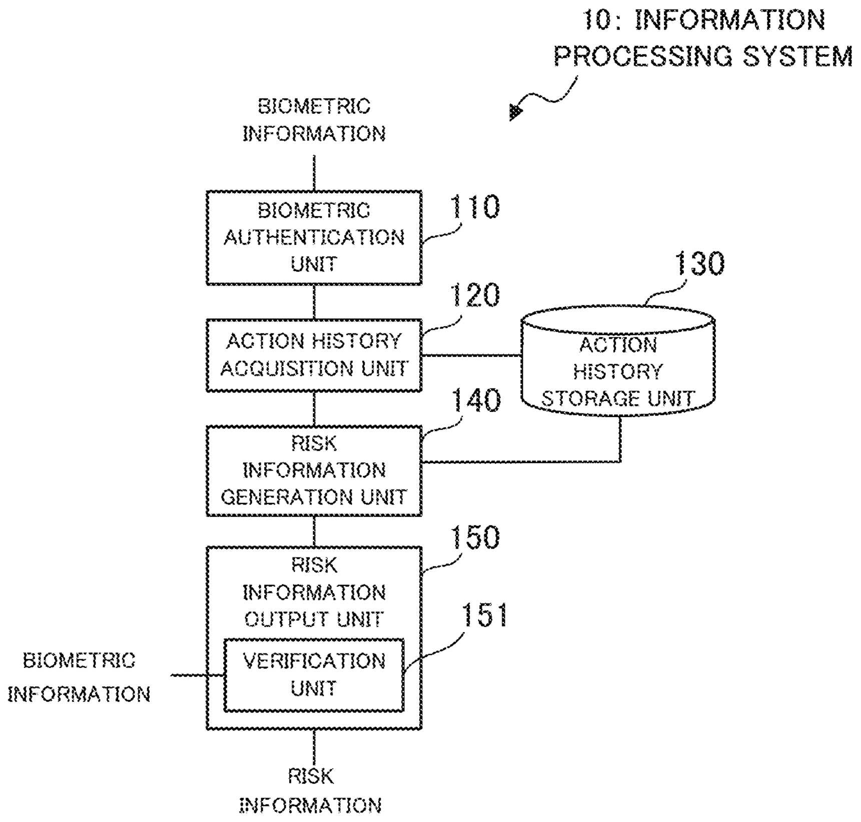
FIG. 5 is a block diagram illustrating a functional configuration of an information processing system according to a second example embodiment.

As illustrated in FIG. 5, the information processing system 10 according to the second example embodiment includes, as components for realizing the functions thereof, the biometric authentication unit 110, the action history acquisition unit 120, the action history storage unit 130, the risk information generation unit 140, and the risk information output unit 150. In particular, the risk information output unit 150 according to the second example embodiment includes a verification unit 151.

The verification unit 151 is configured to perform a collation/verification process by using the biometric information. Specifically, the verification unit 151 is configured to perform the collation/verification (in other words, a process of identifying the first user), by using the biometric information about the first user inputted from the second user. The verification unit 151 may be configured to acquire the biometric information about the first user, from a terminal or the like operated by the second user. For example, the verification unit 151 may acquire an image of the first user captured by a built-in camera from a smart phone owned by the second user, and may acquire the biometric information from the image of the first user. The risk information output unit 150 is configured to output the risk information about the first user in accordance with a collation/verification result of the verification unit 151. That is, the risk information output unit 150 is configured to output the risk information about the first user identified by the collation/verification process.

Output Operation

Next, a flow of the output operation by the information processing system 10 according to the second example embodiment will be described with reference to FIG. 6. FIG. 6 is a flowchart illustrating the flow of the output operation of the information processing system according to the second example embodiment. In FIG. 6, the same steps as those illustrated in FIG. 4 carry the same reference numerals.

Figure 6:
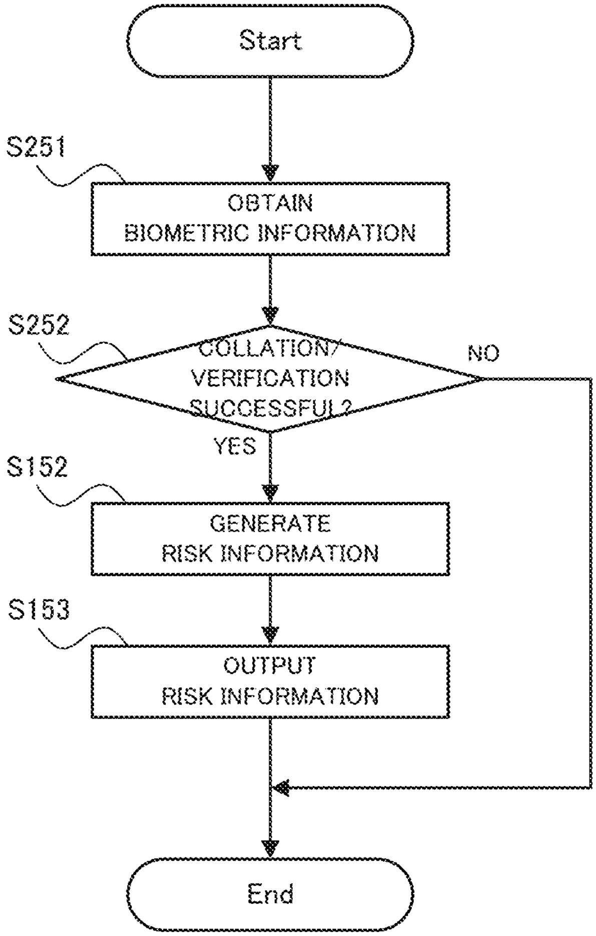
FIG. 6 is a flowchart illustrating a flow of the output operation of the information processing system according to the second example embodiment.

As illustrated in FIG. 6, in the output operation by the information processing system 10 according to the second example embodiment, first, the verification unit 151 acquires the biometric information about the first user (step S251). Then, the verification unit 151 performs the collation/verification process by using the acquired biometric information about the first user (step S252). In the case where the collation/verification process is failed (i.e., the first user cannot be identified) (step S252: NO), the subsequent processing steps are omitted, and a series of the output operation is ended (in this case, the risk information is not outputted).

On the other hand, in the case where the collation/verification process is successful (i.e., the first user can be identified) (step S252: YES), the risk information generation unit 140 reads the action history information about the first user stored in the action history storage unit 130, and generates the risk information about the first user (step S152). Then, the risk information output unit 150 outputs the risk information about the first user (step S153).

Technical Effect

Next, a technical effect acquired by the information processing system 10 according to the second example embodiment will be described.

As described in FIG. 5 and FIG. 6, in the information processing system 10 according to the second example embodiment, the risk information is outputted in accordance with the result of the collation/verification using the biometric information. In this way, even in the case where pieces of the action history information about a plurality of users are stored, it is possible to identify from them the first user who is a target, and to properly output the risk information.

Third Example Embodiment

The information processing system 10 according to a third example embodiment will be described with reference to FIG. 7. The third example embodiment describes a specific example of the action history information handled in the first and second example embodiments, and may be the same as the first and second example embodiments in the configuration and the operation. For this reason, a part that is different from each of the example embodiments described above will be described in detail below, and a description of other overlapping parts will be omitted as appropriate.

Specific Example of Action History Information

First, with reference to FIG. 7, a specific example of the action history information handled by the information processing system 10 according to the third example embodiment will be described. FIG. 7 is a table illustrating an example of the action history information handled by the information processing system according to the third example embodiment.

As illustrated in FIG. 7, the action history information handled by the information processing system 10 according to the third example embodiment may include a movement history, environmental information, human body information, and a conversation history. The action history information may include all of the movement history, the environmental information, the human body information, and the conversation history, or may include at least one of them.

The movement history is information indicating a history of the movement of the first user. The movement history may include, for example, past position information about the user that may be acquired from a GPS (Global Positioning System) or the like, as well as time information about a time when the user visits the location.

The environmental information is information associated with the movement history described above, and is information indicating an environment of the location where the user visits. The environmental information may include, for example, information about air temperature, air pressure, ventilation conditions, and the like.

The human body information is information about the first user. The human body information may include, for example, information such as body temperature and pulse of the first user.

The conversation history is information indicating a history of conversation of the first user. The conversation history may include information about a conversation duration, a conversation target, the presence/absence of a mask when the conversation occurs, and the like.

The various types of information described above are examples, and the action history information may include another type of information that is not mentioned here.

Technical Effect

Next, a technical effect acquired by the information processing system 10 according to the third example embodiment will be described.

As described in FIG. 7, in the information processing system 10 according to the third example embodiment, the action history information includes at least one of the movement history, the environmental information, the human body information, and the conversation history. In this way, it is possible to properly generate the risk information on the basis of the action history information.

Fourth Example Embodiment

The information processing system 10 according to a fourth example embodiment will be described with reference to FIG. 8 and FIG. 9. The fourth example embodiment is partially different from the first to third example embodiments only in the configuration and operation, and may be the same as the first to third example embodiments in the other parts. For this reason, a part that is different from each of the example embodiments described above will be described in detail below, and a description of other overlapping parts will be omitted as appropriate.

Functional Configuration

First, a functional configuration of the information processing system 10 according to the fourth example embodiment will be described with reference to FIG. 8. FIG. 8 is a block diagram illustrating the functional configuration of the information processing system according to the fourth example embodiment. In FIG. 8, the same components as those illustrated in FIG. 2 carry the same reference numerals.

Figure 8:
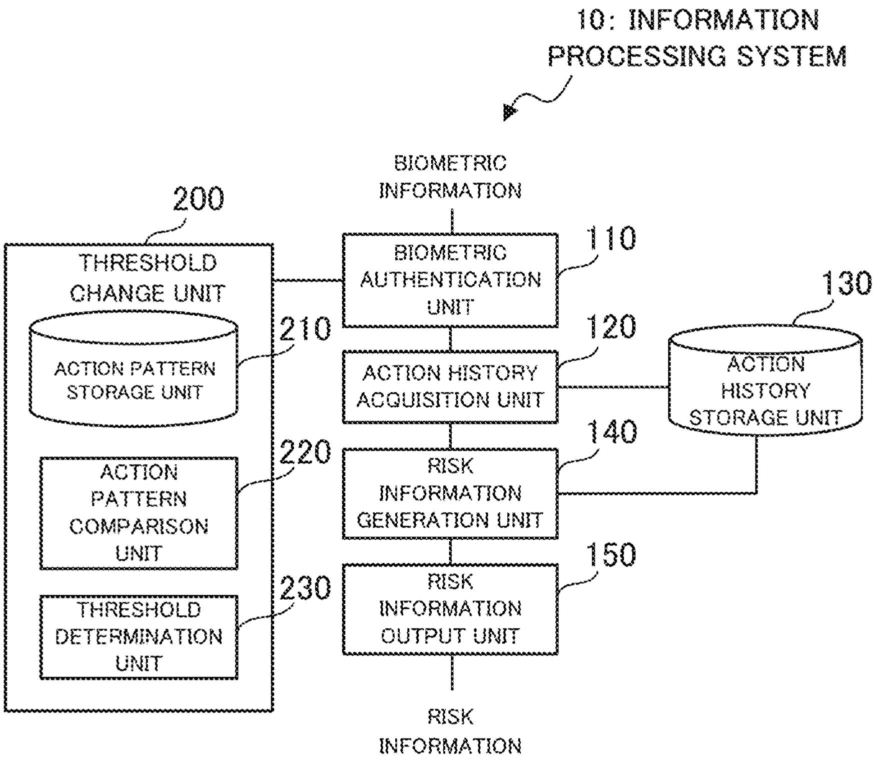
FIG. 8 is a block diagram illustrating a functional configuration of an information processing system according to a fourth example embodiment.

As illustrated in FIG. 8, the information processing system 10 according to the fourth example embodiment includes, as components for realizing the functions thereof, the biometric authentication unit 110, the action history acquisition unit 120, the action history storage unit 130, the risk information generation unit 140, the risk information output unit 150, and a threshold change unit 200. The threshold change unit 200 includes an action pattern storage unit 210, an action pattern comparison unit 220, and a threshold determination unit 230. The action pattern storage unit 210 may be realized or implemented by the storage apparatus 14 (see FIG. 1), for example. Furthermore, each of the action pattern comparison unit 220 and the threshold determination unit 230 may be a processing block realized or implemented by the processor 11 (see FIG. 1), for example.

The action pattern storage unit 210 is configured to store an action pattern of the first user. Here, the "action pattern" is information indicating a daily action pattern and an action tendency of the first user, and may include information about the movement history of the first user, or the like, for example. In addition, the action pattern may at least partially overlap with the action history information. In this case, the action pattern storage unit 210 and the action history storage unit 130 may be configured as a common storage unit.

The action pattern comparison unit 220 is configured to compare an action pattern in a predetermined period of the first user (e.g., an action pattern of the latest day) with a past action pattern (e.g., action patterns of several ten days stored in the past). Then, the action pattern comparison unit 220 is configured to output whether or not the action pattern in the predetermined period matches the past action pattern. The action pattern comparison unit 220 may calculate a degree of similarity of each of the action patterns, thereby to determine whether or not they match, for example.

The threshold determination unit 230 is configured to determine a threshold (specifically, an authentication threshold for determining whether the biometric authentication is successful or failed) of the biometric authentication unit 110, on the basis of a comparison result of the action pattern comparison unit 220. The threshold determination unit 230 determines such a threshold of the biometric authentication unit 110 that causes the biometric authentication to be hardly successful, in the case where the action pattern in the predetermined period does not match the past action pattern. The threshold change unit 200 reflects the threshold determined by the threshold determination unit 230 in the biometric authentication unit 110 (i.e., changes the threshold).

Threshold Change Operation

Next, with reference to FIG. 9, a flow of an operation of changing the threshold of the biometric authentication (hereinafter referred to as a "threshold change operation" as appropriate) by the information processing system 10 according to the fourth example embodiment will be described. FIG. 9 is a flowchart illustrating the flow of the threshold change operation of the information processing system according to the fourth example embodiment. A series of processing steps illustrated in FIG. 9 is assumed to be started in the case where the action pattern storage unit 210 sufficiently stores the action patterns.

Figure 9:
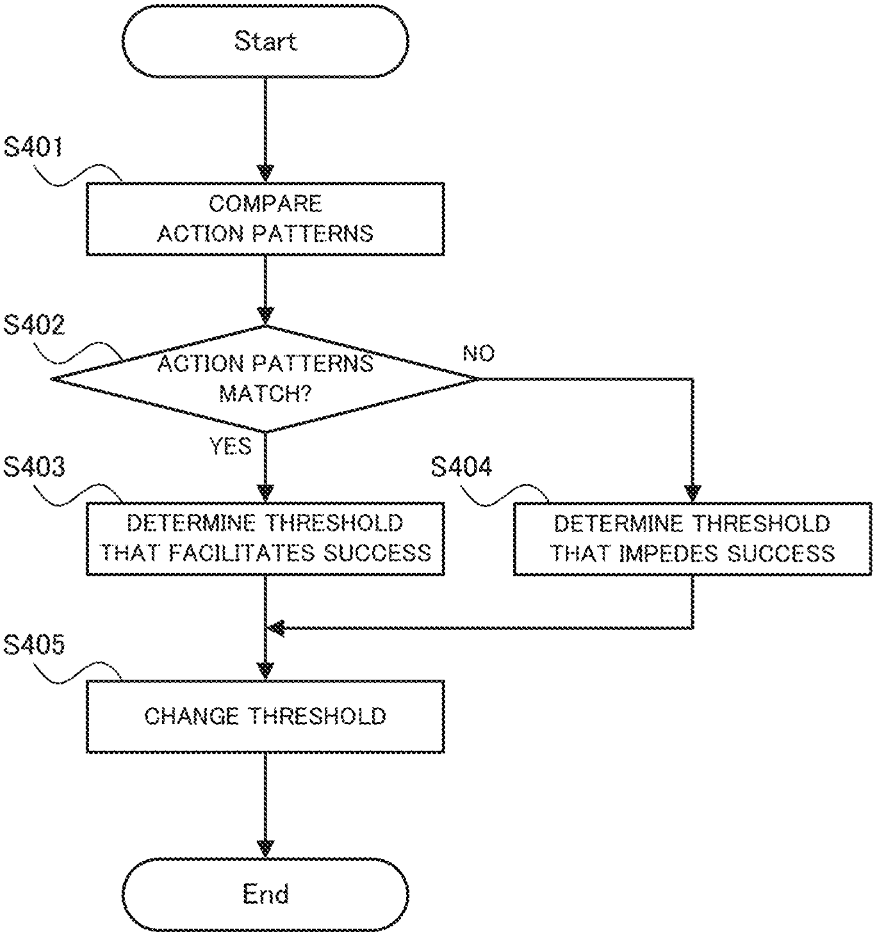
FIG. 9 is a flowchart illustrating a flow of a threshold change operation of the information processing system according to the fourth example embodiment.

As illustrated in FIG. 9, in the threshold change operation by the information processing system 10 according to the fourth example embodiment, first, the action pattern comparison unit 220 compares the action pattern in the predetermined period with the past action pattern (step S401). Then, the threshold determination unit 230 determines whether or not the action pattern in the predetermined period matches the past action pattern, from the comparison result of the action pattern (step S402).

Subsequently, in the case where the action pattern in the predetermined period matches the past action pattern (step S402: YES), the threshold determination unit 230 determines that the first user is likely to be a legitimate person (i.e., a person who shows the past action pattern), and determines such a threshold that causes the biometric authentication to be easily successful (step S403). On the other hand, in the case where the action pattern in the predetermined period does not match the past action pattern (step S402: NO), the threshold determining unit 230 determines that the first user is unlikely to be the legitimate person, and determines such a threshold that causes the biometric authentication to be hardly successful (step S404).

Subsequently, the threshold change unit 200 changes the threshold used in the biometric authentication unit 110 to the threshold determined by the threshold determination unit 230 (step S405).

Technical Effect

Next, a technical effect acquired by the information processing system 10 according to the fourth example embodiment will be described.

As described in FIG. 8 and FIG. 9, in the information processing system 10 according to the fourth example embodiment, the threshold of the biometric authentication is changed in accordance with the action pattern of the user. In this way, it is possible to change the ease of success in the biometric authentication, on the basis of the possibility that the first user is a legitimate person, which is estimated from the action pattern. As a result, it is possible to perform the biometric authentication with higher accuracy, and it is possible to prevent injustice such as spoiling, for example.

Fifth Example Embodiment

The information processing system 10 according to a fifth example embodiment will be described with reference to FIG. 10 and FIG. 11. The fifth example embodiment is partially different from the first to fourth example embodiments only in the configuration and operation, and may be the same as the first to fourth example embodiments in the other parts. For this reason, a part that is different from each of the example embodiments described above will be described in detail below, and a description of other overlapping parts will be omitted as appropriate.

Functional Configuration

First, a functional configuration of the information processing system 10 according to the fifth example embodiment will be described with reference to FIG. 10. FIG. 10 is a block diagram illustrating the functional configuration of the information processing system according to the fifth example embodiment. In FIG. 10, the same components as those illustrated in FIG. 2 carry the same reference numerals.

Figure 10:
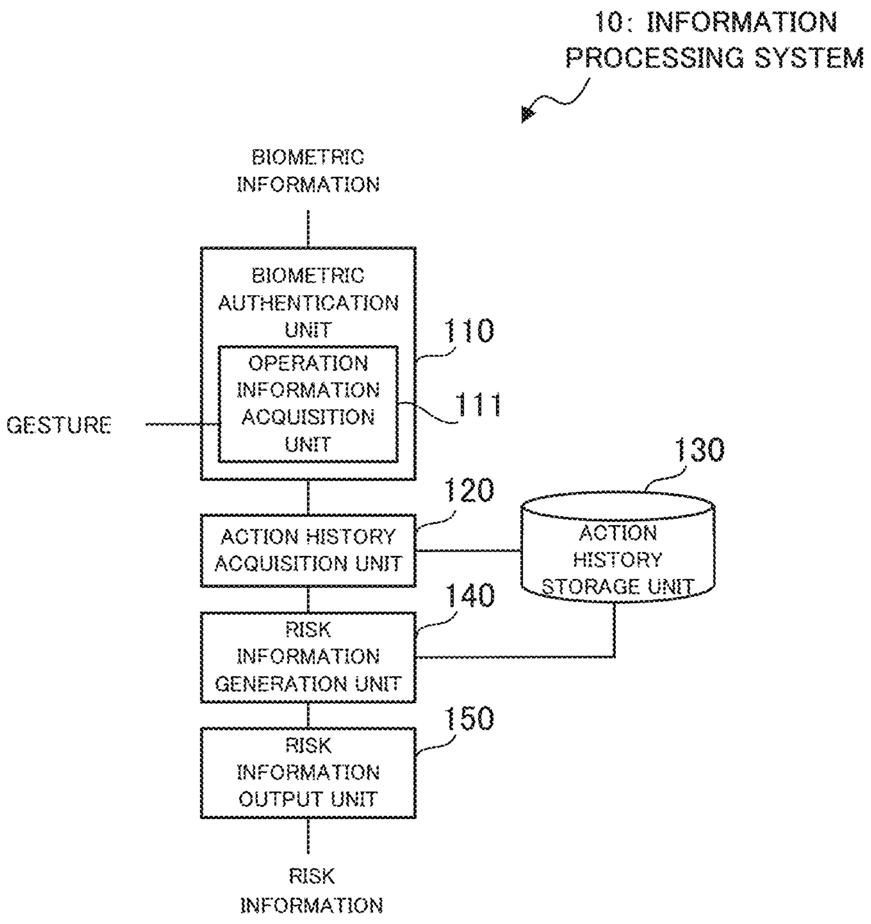
FIG. 10 is a block diagram illustrating a functional configuration of an information processing system according to a fifth example embodiment.

As illustrated in FIG. 10, the information processing system 10 according to the fifth example embodiment includes, as components for realizing the functions thereof, the biometric authentication unit 110, the action history acquisition unit 120, the action history storage unit 130, the risk information generation unit 140, and the risk information output unit 150. Then, the biometric authentication unit 110 according to the fifth example embodiment especially includes an operation information acquisition unit 111

The operation information acquisition unit 111 is configured to detect a gesture performed around a shielding object (e.g., a mask, sunglasses, a hat, etc.) that partially covers a face of the first user and to acquire operation information corresponding to the gesture, in the case where the biometric authentication of the first user is performed. The operation information acquisition unit 111 may include, for example, a camera, and may detect an action of bringing a finger to a position that overlaps the mask, as the gesture. The operation information acquisition unit 111 may detect the gesture on the basis of a difference between frames of a plurality of images (e.g., a change in a skin color area, etc.), for example.

The operation information acquired by the operation information acquisition unit 111 is used for a biometric authentication process by the biometric authentication unit 110. How to use the operation information in the biometric authentication is not particularly limited. For example, the operation information may be directly used for the authentication process as in the biometric information, or may be used as supplemental information for properly performing the authentication process.

Biometric Authentication Operation

Next, with reference to FIG. 11, a flow of an operation in the case where the biometric authentication is performed (hereinafter referred to as a "biometric authentication operation" as appropriate) by the information processing system 10 according to the fifth example embodiment will be described. FIG. 11 is a flowchart illustrating the flow of the biometric authentication operation of the information processing system according to the fifth example embodiment.

Figure 11:
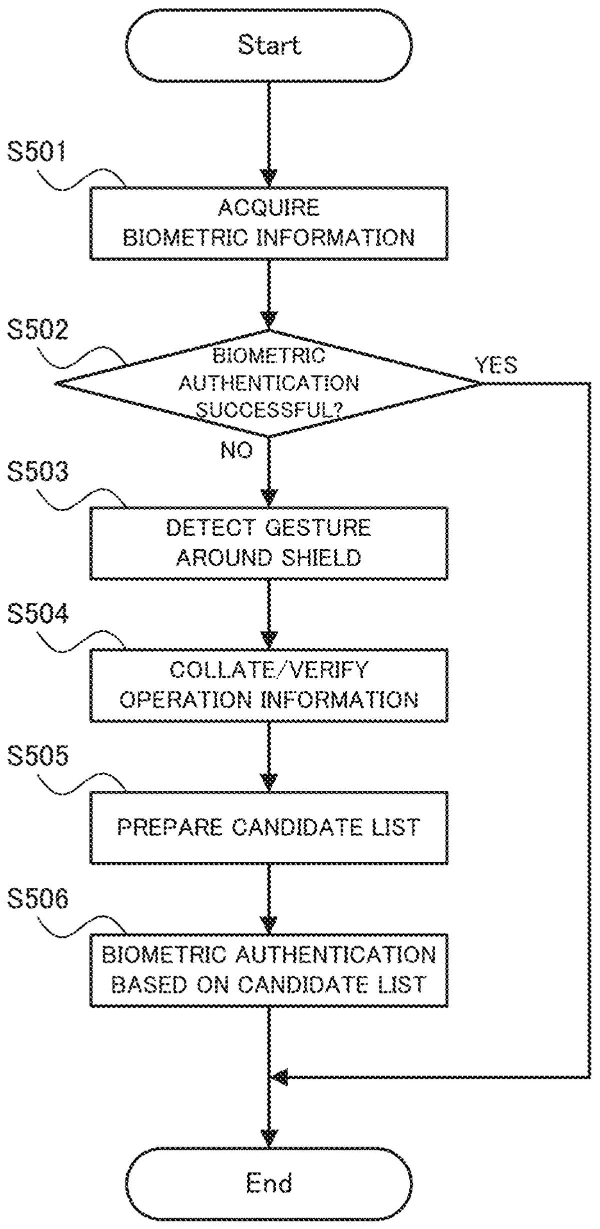
FIG. 11 is a flowchart illustrating a flow of a biometric authentication operation of the information processing system according to the fifth example embodiment.

As illustrated in FIG. 11, in the biometric authentication operation by the information processing system 10 according to the fifth example embodiment, first, the biometric authentication unit 110 acquires the biometric information about the first user (step S501). Then, the biometric authentication unit 110 performs the biometric authentication by using the acquired biometric information (step S502). In the case where the biometric authentication is successful at this stage (step S502: YES), the subsequent processing steps are omitted, and a series of the biometric authentication operation is ended (i.e., the process related to the operation information is not performed).

On the other hand, in the case where the biometric authentication is failed (step S502: NO), the operation information acquisition unit 111 detects the gesture performed around the shielding object and acquires the operation information (step S503). Then, the biometric authentication unit 110 collates/verifies the acquired operation information with the operation information registered in advance (step S504). Here, the operation information to be collated/verified is assumed to be registered in accordance with the operation performed by each user in user registration.

Subsequently, the biometric authentication unit 110 prepares a candidate list on the basis of a collation/verification result of the operation information (step S505). Specifically, the biometric authentication unit 110 prepares a list of the users for whom the operation information matches the operation information registered in advance (i.e., the users who have registered the same gesture as the one detected this time). Then, the biometric authentication unit 110 narrows down an authentication target to the users included in the candidates list, and performs the biometric authentication again (step S506). The biometric authentication here may be performed by using another type of biometric information that is different from the biometric information acquired in the step S501 (e.g., by acquiring the biometric information from a newly captured image).

In the above example, after the biometric authentication is failed, the operation information is supplementally used; however, the authentication process may be performed by using the operation information from the beginning. For example, at a first stage, two-element authentication may be performed by using both the biometric information and the operation information. In addition, liveness determination may be performed from the gesture or the movement associated with the gesture.

Technical Effect

Next, a technical effect acquired by the information processing system 10 according to the fifth example embodiment will be described.

As described in FIG. 10 and FIG. 11, in the information processing system 10 according to the fifth example embodiment, the operation information acquired by detecting the gesture performed around the shielding object is used in the biometric authentication operation. In this way, even in the case where the first user wears the shielding object, it is possible to perform the biometric authentication with high accuracy by using the presence of the shielding object for the gesture detection.

Sixth Example Embodiment

The information processing system 10 according to a sixth example embodiment will be described with reference to FIG. 12 and FIG. 13. The sixth example embodiment is partially different from the fifth example embodiment only in the configuration and operation, and may be the same as the fifth example embodiment in the other parts. For this reason, a part that is different from each of the example embodiments described above will be described in detail below, and a description of other overlapping parts will be omitted as appropriate.

Functional Configuration

First, a functional configuration of the information processing system 10 according to the sixth example embodiment will be described with reference to FIG. 12. FIG. 12 is a block diagram illustrating the functional configuration of the information processing system according to the sixth example embodiment. In FIG. 12, the same components as those illustrated in FIG. 10 carry the same reference numerals.

Figure 12:
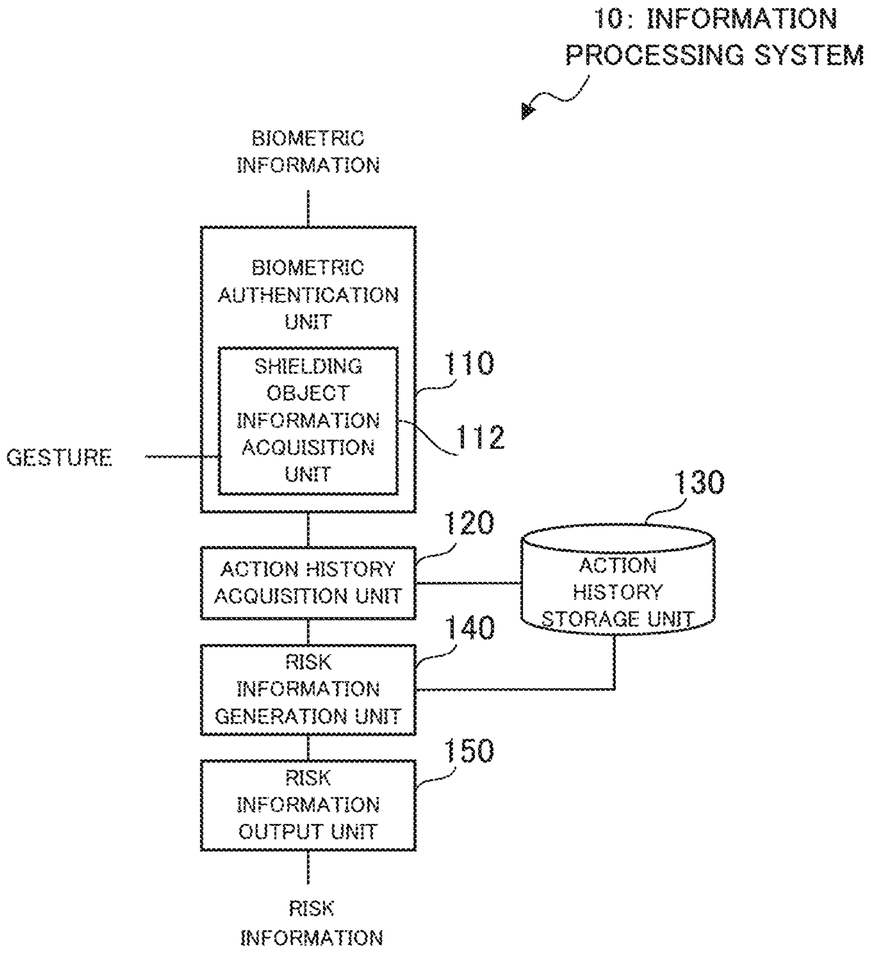
FIG. 12 is a block diagram illustrating a functional configuration of an information processing system according to a sixth example embodiment.

As illustrated in FIG. 12, the information processing system 10 according to the sixth example embodiment includes, as components for realizing the functions thereof, the biometric authentication unit 110, the action history acquisition unit 120, the action history storage unit 130, the risk information generation unit 140, and the risk information output unit 150. Then, the biometric authentication unit 110 according to the sixth example embodiment especially includes a shielding object information acquisition unit 112.

The shielding object information acquisition unit 112 is configured to detect a change in at least one of a surface area and a position of the shielding object that partially covers the face of the first user, in the case where the biometric authentication of the first user is performed, and to acquire shielding object information corresponding to the change of the shielding object. The shielding object information acquisition unit 112 includes, for example, a camera, and may detect a change in at least one of a surface area and a position of a mask, in the case where the mask is moved down. The shielding object information acquisition unit 112 may detect the change in at least one of the surface area and the position of the shielding object, on the basis of a difference between frames of a plurality of images, for example.

The shielding object information acquired by the shielding object information acquisition unit 112 is used for the biometric authentication process by the biometric authentication unit 110. How to use the shielding object information in the biometric authentication is not particularly limited. For example, the shielding object information may be directly used for the authentication process as in the biometric information, or may be used as supplemental information for properly performing the authentication process.

Biometric Authentication Operation

Next, with reference to FIG. 13, a flow of the biometric authentication operation by the information processing system 10 according to the sixth example embodiment will be described. FIG. 13 is a flowchart illustrating the flow of the biometric authentication operation of the information processing system according to the sixth example embodiment. In FIG. 13, the same steps as those illustrated in FIG. 11 carry the same reference numerals.

Figure 13:
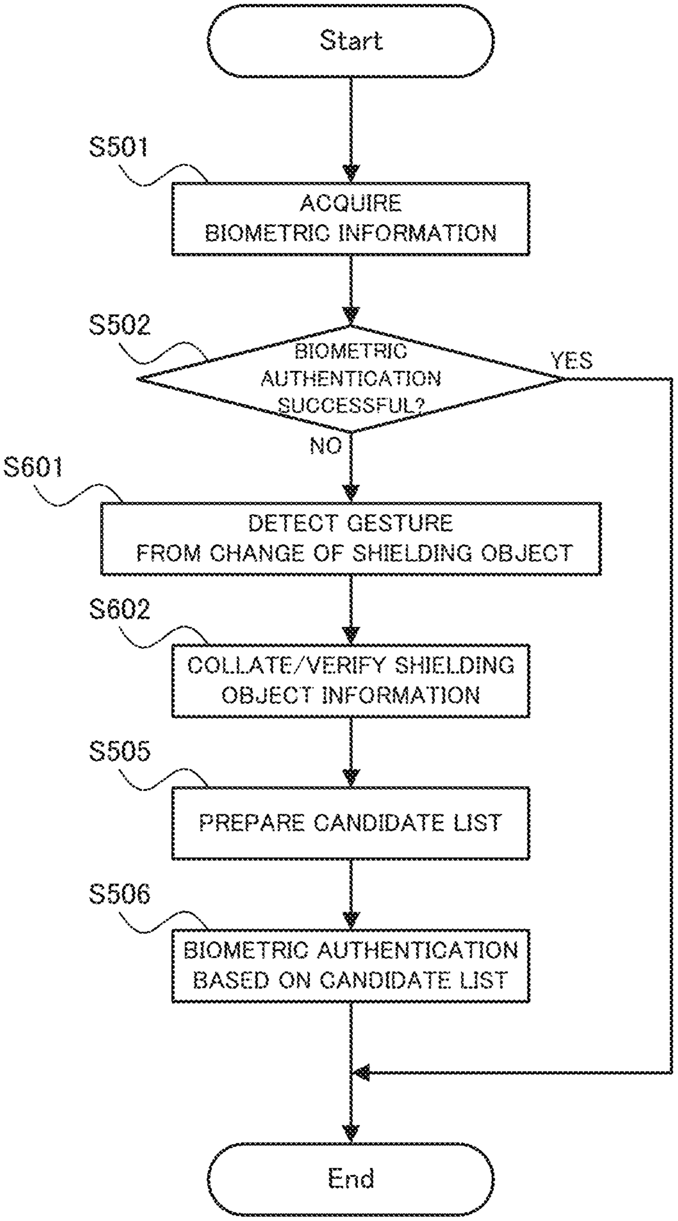
FIG. 13 is a flowchart illustrating a flow of the biometric authentication operation of the information processing system according to the sixth example embodiment.

As illustrated in FIG. 13, in the biometric authentication operation by the information processing system 10 according to the sixth example embodiment, first, the biometric authentication unit 110 acquires the biometric information about the first user (step S501). Then, the biometric authentication unit 110 performs the biometric authentication by using the acquired biometric information (step S502). In the case where the biometric authentication is successful at this stage (step S502: YES), the subsequent processing steps are omitted, and a series of the biometric authentication operation is ended (i.e., the process related to the operation information is not performed).

On the other hand, in the case where the biometric authentication is failed (step S502: NO), the shielding object information acquisition unit 112 detects the change in the surface area or the position of the shielding object, and acquires the shielding object information (step S601).

Then, the biometric authentication unit 110 collates/verifies the acquired shielding object information with the shielding object information registered in advance (step S602). Here, the shielded object information to be collated/verified is assumed to be registered in accordance with the operation performed by each user in the user registration.

Subsequently, the biometric authentication unit 110 prepares a candidate list on the basis of a collation/verification result of the shielding object information (step S505). Specifically, the biometric authentication unit 110 prepares a list of the users for whom the shielding object information matches the shielding object information registered in advance (i.e., the users who have registered the operation that allows the same change as that of the shielding object detected this time). Then, the biometric authentication unit 110 narrows down an authentication target to the users included in the candidates list, and performs the biometric authentication again (step S506). The biometric authentication here may be performed by using another type of biometric information that is different from the biometric information acquired in the step S501 (e.g., by acquiring the biometric information from a newly captured image).

In the above example, after the biometric authentication is failed, the shielding object information is supplementally used; however, the authentication process may be performed by using the shielding object information from the beginning. For example, at a first stage, two-element authentication may be performed by using both the biometric information and the shielding object information. In addition, the liveness determination may be performed from an operation in the case where the shielding object is changed, or an operation associated with the aforementioned operation.

Technical Effect

Next, a technical effect acquired by the information processing system 10 according to the sixth example embodiment will be described.

As described in FIG. 12 and FIG. 13, in the information processing system 10 according to the sixth example embodiment, the shielding object information acquired by detecting the change of the shielding object is used in the biometric authentication operation. In this way, even in the case where the first user wears the shielding object, it is possible to perform the biometric authentication with high accuracy, by using the movement of the shielding object for the authentication.

Seventh Example Embodiment

The information processing system 10 according to a seventh example embodiment will be described with reference to FIG. 14 to FIG. 16. The seventh example embodiment is partially different from the first to sixth example embodiments only in the configuration and operation, and may be the same as the first to sixth example embodiments in the other parts. For this reason, a part that is different from each of the example embodiments described above will be described in detail below, and a description of other overlapping parts will be omitted as appropriate.

Functional Configuration

First, a functional configuration of the information processing system 10 according to the seventh example embodiment will be described with reference to FIG. 14. FIG. 14 is a block diagram illustrating the functional configuration of the information processing system according to the seventh example embodiment. In FIG. 14, the same components as those illustrated in FIG. 2 carry the same reference numerals.

Figure 14:
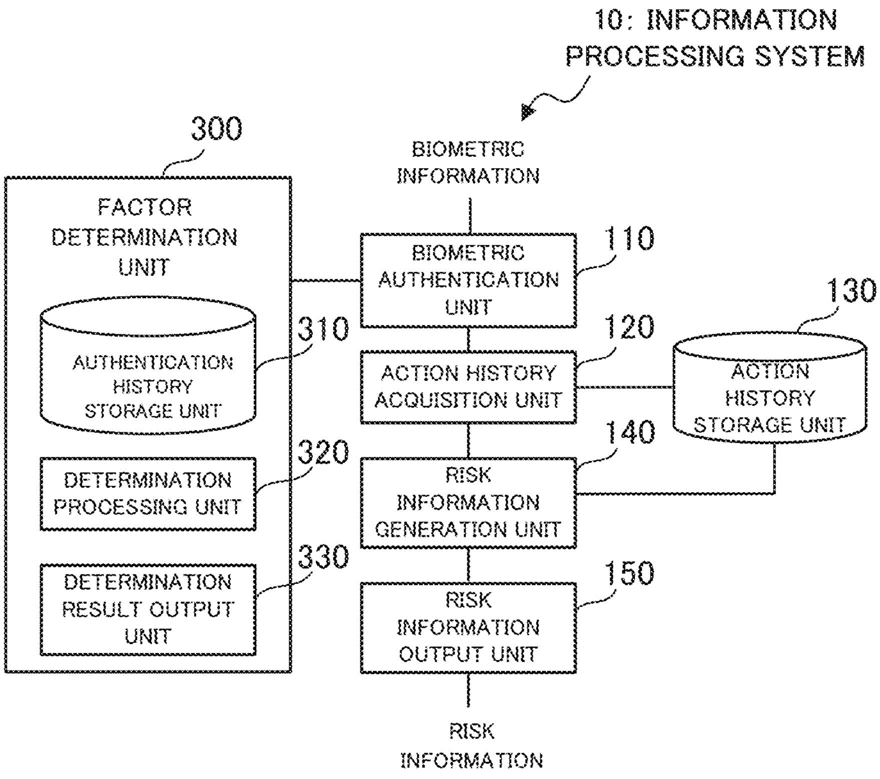
FIG. 14 is a block diagram illustrating a functional configuration of an information processing system according to a seventh example embodiment.

As illustrated in FIG. 14, the information processing system 10 according to the seventh example embodiment includes, as components for realizing the functions thereof, the biometric authentication unit 110, the action history acquisition unit 120, the action history storage unit 130, the risk information generation unit 140, the risk information output unit 150, and a factor determination unit 300. The factor determination unit 300 includes an authentication history storage unit 310, a determination processing unit 320, and a determination result output unit 330. The authentication history storage unit 310 may be realized or implemented by the storage apparatus 14 (see FIG. 1), for example. Each of the determination processing unit 320 and the determination result output unit 330 may be a processing block realized or implemented by the processor 11 (see FIG. 1), for example.

The authentication history storage unit 310 is configured to be store a past authentication history in the biometric authentication unit 110. The authentication history storage unit 310 is configured to store not only information indicating the success or failure of the authentication, but also a value used in the authentication (e.g., a degree of matching between feature quantities, etc.), as the history.

The determination processing unit 320 is configured to determine whether or not a factor of occurrence of false rejection in the biometric authentication is caused by an input condition of the biometric information (e.g., an apparatus or an environment for reading the biometric information), or by a change with time in the biometric information (e.g., a change in the face due to aging, etc.), by using the past authentication history stored in the authentication history storage unit 310.

The determination result output unit 330 is configured to output a determination result by the determination processing unit 320 (i.e., the factor of the occurrence of the false rejection in the biometric authentication). The determination result output unit 330 may output such a result that the factor of the occurrence of the false rejection is specified to one of the two, or may output information indicating the possibility that the factor of the occurrence of the false rejection is the input condition of the biometric information, and the possibility that the factor of the occurrence of the false rejection is the change with time in the biometric information (e.g., ratio information). The determination result output unit 330 may be configured to output instruction information for performing a particular process corresponding to the determination result. For example, the determination result output unit 330 may be configured to output information for performing a process to improve the factor of the occurrence of the false rejection.

Factor Determination Operation

Next, with reference to FIG. 15, a flow of an operation in the case where a factor of an authentication error is determined (hereinafter referred to as a "factor determination operation" as appropriate) by the information processing system 10 according to the seventh example embodiment will be described. FIG. 15 is a flowchart illustrating the flow of the factor determination operation of the information processing system according to the seventh example embodiment. The factor determination operation may be performed at a timing when the false rejection actually occurs, or may be performed at a timing when the possibility of occurrence of the false rejection is determined to be high.

Figure 15:
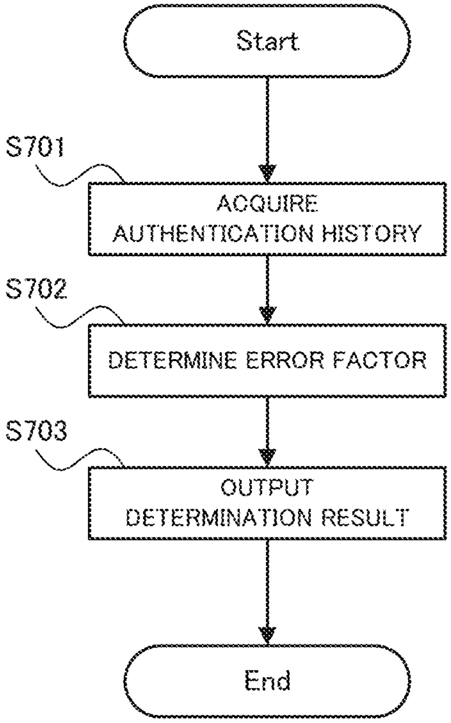
FIG. 15 is a flowchart illustrating a flow of a factor determination operation of the information processing system according to the seventh example embodiment.

As illustrated in FIG. 15, in the factor determination operation by the information processing system 10 according to the seventh example embodiment, first, the determination processing unit 320 acquires the past authentication history from the authentication history storage unit 310 (step S701).

Subsequently, the determination processing unit 320 determines the factor of the occurrence of the false rejection, from the acquired past authentication history (step S702). The determination processing unit 320 may determine the factor of the occurrence of the false rejection in accordance with a change tendency of the authentication history, for example. A more detailed determination method will be described later with a specific example.

Subsequently, the determination result output unit 330 outputs the determination result of the determination processing unit 320 (step S703). The determination result output unit 330 may perform the output by using the output apparatus 16 described above, for example.

The determination result output unit 330 may output information encouraging the user to change the input condition of the biometric information, in the case where the factor of the occurrence of the false rejection is the input condition of the biometric information. For example, the determination result output unit 330 may output information encouraging the user to change a direction of a camera or a lighting device, or information encouraging the user to renew the apparatus itself. In addition, the determination result output unit 330 may output information encouraging the user to update the biometric information, in the case where the factor of the occurrence of the false rejection is the change with time in the biometric information. For example, the determination result output unit 330 may output information encouraging the user to capture a new photograph to be used for the biometric authentication.

Specific Determination Example

Next, a determination method in the factor determination operation will be described with reference to FIG. 16 with a specific example. FIG. 16 is a graph illustrating an example of authentication history information handled by the information processing system according to the seventh example embodiment.

Figure 16:
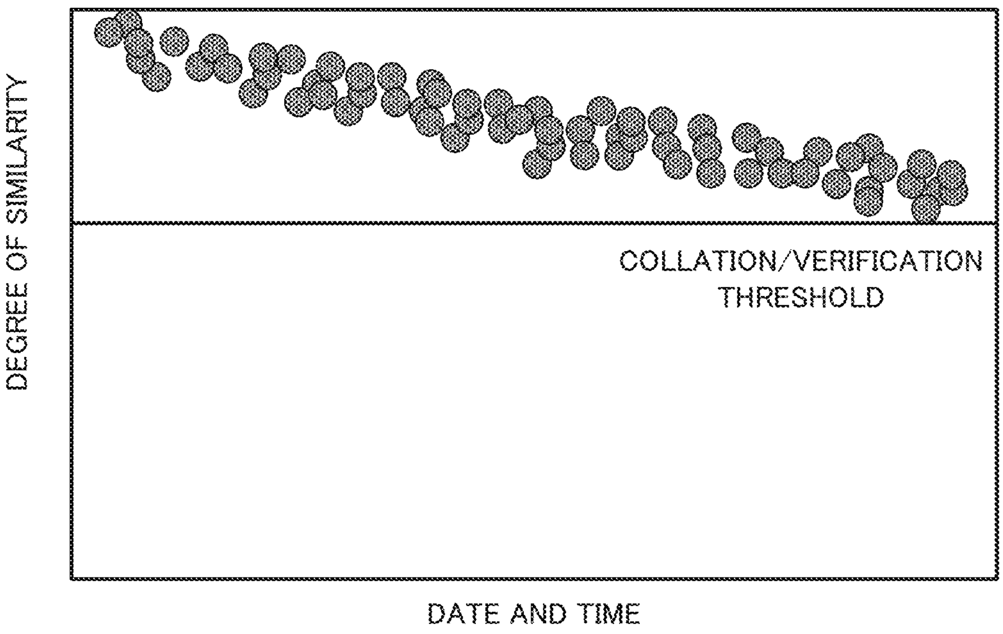
FIG. 16 is a graph illustrating an example of authentication history information handled by the information processing system according to the seventh example embodiment.

In the example illustrated in FIG. 16, in the case where a degree of similarity of the biometric information (i.e., a degree of similarity between the biometric information acquired for the authentication and the registered biometric information) exceeds a collation/verification threshold, the authentication is determined to be successful. As can be seen from the drawing, the degree of similarity of the biometric information decreases as the date and time elapses, and approaches the collation/verification threshold. In such a situation, the false rejection is likely to occur.

Here, in the example illustrated in FIG. 16, the degree of similarity gradually decreases in a constant tendency. In such a case, it can be determined that the factor of the occurrence of the false rejection is likely to be the change with time in the biometric information. On the other hand, in the case where the input condition of the biometric information is the factor, the degree of similarity is estimated to change relatively steeply. Therefore, in such a case, it may be determined that the factor of the occurrence of the false rejection is likely to be the change with time in the biometric information.

The determination method described above is merely an example, and other criteria may be used to determine the factor of the occurrence of the false rejection. Specifically, it is sufficient to register in advance information for associating the change tendency of the authentication history with the factor of the occurrence of the false rejection.

Technical Effect

Next, a technical effect acquired by the information processing system 10 according to the seventh example embodiment will be described.

As described in FIG. 14 to FIG. 16, in the information processing system 10 according to the seventh example embodiment, the factor of the occurrence of the false rejection is determined on the basis of the past authentication history. In this way, it is possible to quickly and accurately understand the factor of the occurrence of the false rejection. Therefore, it is possible to take remedial measures to prevent the occurrence of the false rejection, and it is possible to prevent deterioration of authentication accuracy.

Eighth Example Embodiment

The information processing system 10 according to an eighth example embodiment will be described with reference to FIG. 17 to FIG. 19B. The eighth example embodiment is partially different from the first to seventh example embodiments only in the configuration and operation, and may be the same as the first to seventh example embodiments in the other parts. For this reason, a part that is different from each of the example embodiments described above will be described in detail below, and a description of other overlapping parts will be omitted as appropriate.

Functional Configuration

Figure 17:
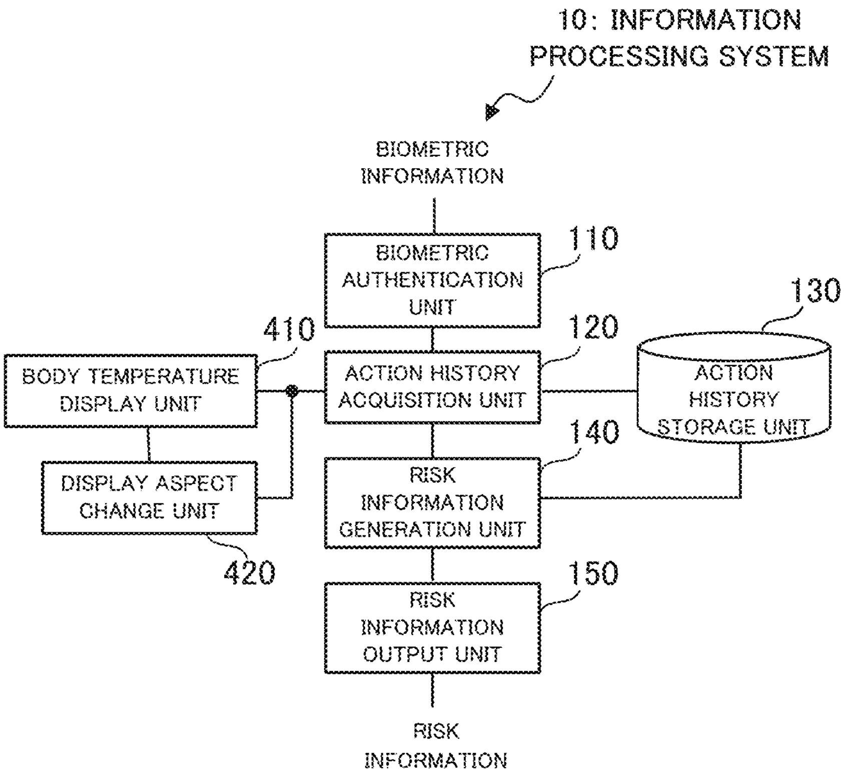
FIG. 17 is a block diagram illustrating a functional configuration of an information processing system according to an eighth example embodiment.

First, a functional configuration of the information processing system 10 according to the eighth example embodiment will be described with reference to FIG. 17. FIG. 17 is a block diagram illustrating the functional configuration of the information processing system according to the eighth example embodiment. In FIG. 17, the same components as those illustrated in FIG. 2 carry the same reference numerals.

As illustrated in FIG. 17, the information processing system 10 according to the eighth example embodiment includes, as components for realizing the functions thereof, the biometric authentication unit 110, the action history acquisition unit 120, the action history storage unit 130, the risk information generation unit 140, the risk information output unit 150, a body temperature display unit 410, and a display aspect change unit 420. The body temperature display unit 410 may be realized or implemented by the output apparatus 16 (see FIG. 1), for example. The display aspect change unit 420 may be a processing block realized or implemented by the processor 11 (see FIG. 1), for example.

The body temperature display unit 410 is configured to display the body temperature of the first user acquired as the action history information. In addition to the body temperature of the first user, the body temperature display unit 410 may be configured to display the image of the first user and another type of user information (e.g., information such as name, age, and attribute). The body temperature display unit 410 is installed or mounted such that the body temperature of the first user can be visually recognized by a user other than the first user (e.g., a subsequent user) or a system manager/administrator or the like, for example.

The display aspect change unit 420 is configured to change a display aspect of the body temperature display unit 410 in accordance with a measurement result of the body temperature. The display aspect change unit 420 may be configured to change the display aspect of the body temperature display unit 410 in accordance with whether or not the measured body temperature is greater than or equal to a predetermined value, for example. The predetermined value here may be a threshold for determining heat generation, for example. The display aspect change unit 420 may be configured to select a display aspect corresponding to the measurement result of the body temperature, from a plurality of display aspects registered in advance. The details of the display aspect will be described later with a specific example.

Body Temperature Measurement Operation

Figure 18:
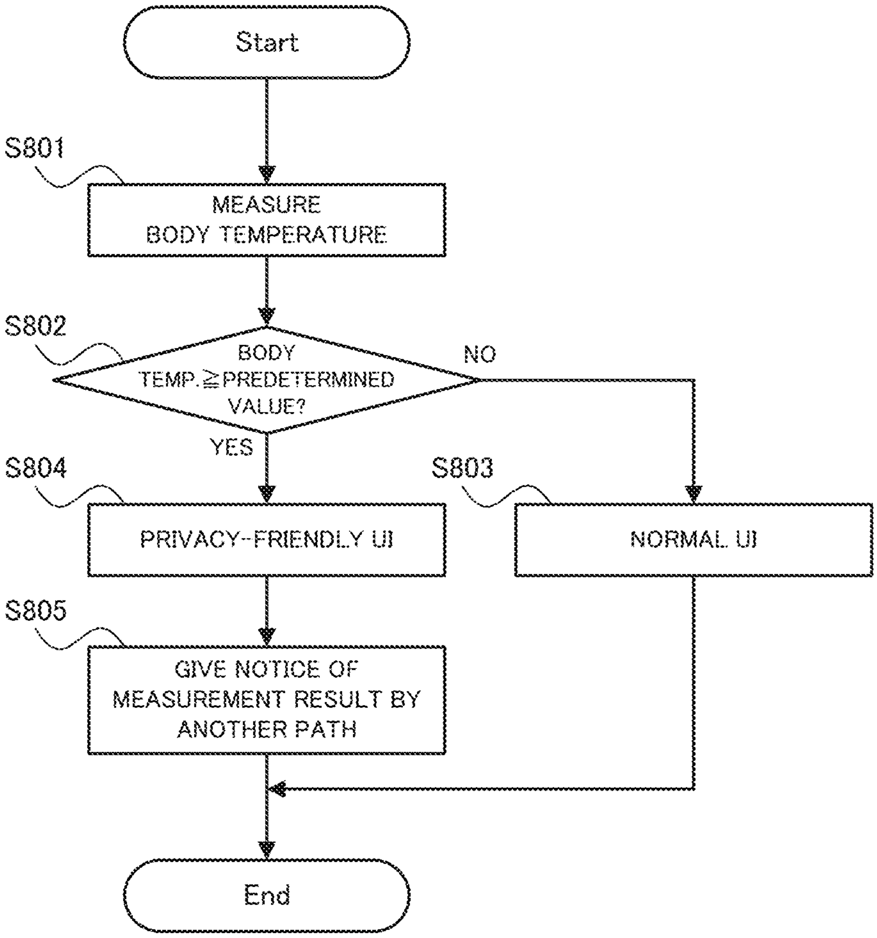
FIG. 18 is a flowchart illustrating a flow of a body temperature measurement operation of the information processing system according to the eighth example embodiment.

Next, a flow of an operation in the case where the body temperature is measured and displayed (hereinafter referred to as a "body temperature measurement operation" as appropriate) by the information processing system 10 according to the eighth example embodiment will be described with reference to FIG. 18. FIG. 18 is a flowchart illustrating the flow of the body temperature measurement operation of the information processing system according to the eighth example embodiment.

As illustrated in FIG. 18, in the body temperature measurement operation by the information processing system 10 according to the eighth example embodiment, first, the body temperature of the first user is measured (step S801). Then, the display aspect change unit 420 determines whether or not the measured body temperature of the first user is greater than or equal to the predetermined value (step S802).

In the case where the body temperature of the first user is not greater than or equal to the predetermined value (step S802: NO), the display aspect change unit 420 changes the display aspect of the body temperature display unit 410 to perform display in a normal UI. On the other hand, in the case where the body temperature of the first user is greater than or equal to the predetermined value (step S802: YES), the display aspect change unit 420 changes the display aspect of the body temperature display unit 410 to perform display in a privacy-friendly UI (step S804). The privacy-friendly UI may be, for example, a display aspect of displaying less information than that in the normal UI. Specifically, the privacy-friendly UI may not directly display the body temperature of the first user.

In the case of the privacy-friendly UI, the body temperature display unit 10 gives notice of the body temperature measured by another path (step S805). The body temperature display unit 410 does not directly display information about the measured body temperature, but transmits the information to another terminal of a notification destination (specifically, a terminal that can be viewed only by a target to be notified), thereby give notice of the measurement result, for example.

Specific Display Examples

Figure 19A:
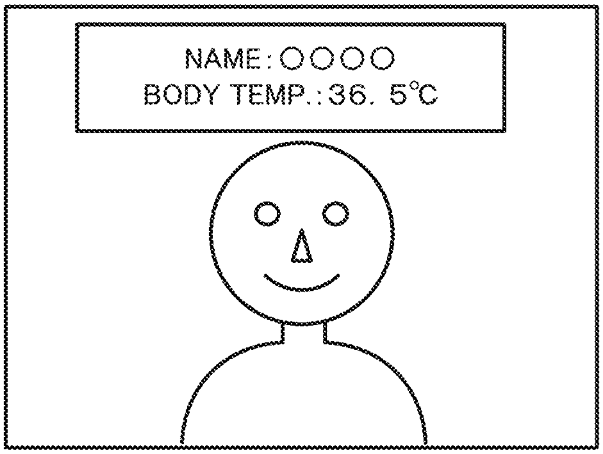
FIG. 19A and FIG. 19B are plan views illustrating display examples of a measurement result by the information processing system according to the eighth example embodiment.
Figure 19B:
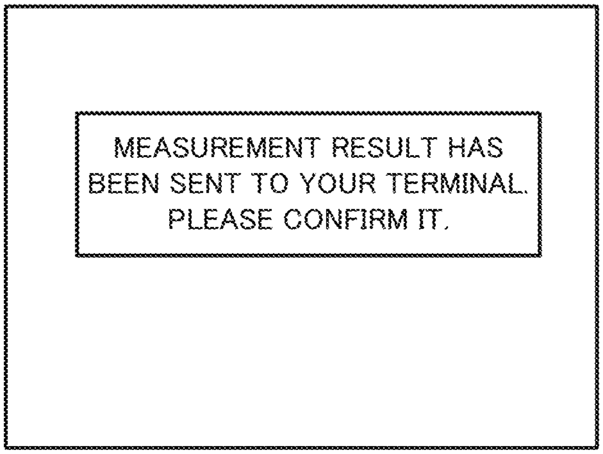

Next, with reference to FIG. 19A and FIG. 19B, the display aspect in the body temperature measurement operation will be described with specific examples. FIG. 19A and FIG. 19B are plan views illustrating display examples of the measurement result by the information processing system according to the eighth example embodiment.

FIG. 19A illustrates the normal UI. In the normal UI, the name and body temperature of the first user are displayed on the image of the first user. The normal UI may be capable of easily displaying the measured results, but there is a risk that personal information about the first user may be known to a person other than the first user. Such a display aspect is not preferable in the case where the first user has a fever (e.g., has a high risk of being infected with an infectious disease), for example.

FIG. 19B illustrates the privacy-friendly UI. The privacy-friendly UI usually does not display the personal information such as the image, name, and body temperature of the first user. Instead, a message "Measurement result has been sent to your terminal. Please confirm it." is displayed. The measured body temperature may be transmitted to a smartphone owned by the first user, for example. At this time, push notification may be performed. According to such a privacy-friendly UI, it is possible to give notice of the measured body temperature without letting others know the personal information about the first user.

The privacy-friendly UI is designed not to display all pieces of the information displayed in the normal UI; however, it may employ such a display aspect that a part of the information is displayed as it is and only the information that is closely related to the privacy is not displayed, for example. Furthermore, the above example describes such a configuration that the two display aspects (i.e., the normal UI and the privacy-friendly UI) are selectively used in accordance with the body temperature, but three or more display aspects may be selectively used, for example. For example, such a display aspect that information to be display gradually decreases little by little with increasing body temperature, may be employed.

Technical Effect

Next, a technical effect acquired by the information processing system 10 according to the eighth example embodiment will be described.

As described in FIG. 17 to FIG. 19, in the information processing system 10 according to the eighth example embodiment, the UI in the case where the body temperature is displayed, is changed on the basis of the measurement result of the body temperature. In this way, it is possible to perform appropriate display considering the privacy of the first user.

A processing method in which a program for allowing the configuration in each of the example embodiments to operate so as to realize the functions in each example embodiment is recorded on a recording medium, and in which the program recorded on the recording medium is read as a code and is executed on a computer, is also included in the scope of each of the example embodiments. That is, a computer-readable recording medium is also included in the range of each of the example embodiments. Not only the recording medium on which the above-described program is recorded, but also the program itself is also included in each example embodiment.

The recording medium to use may be, for example, a floppy disk (registered trademark), a hard disk, an optical disk, a magneto-optical disk, a CD-ROM, a magnetic tape, a nonvolatile memory card, or a ROM. Furthermore, not only the program that is recorded on the recording medium and executes processing alone, but also the program that operates on an OS and executes processing in cooperation with the functions of expansion boards and another software, is also included in the scope of each of the example embodiments.

SUPPLEMENTARY NOTES

The example embodiments described above may be further described as, but not limited to, the following Supplementary Notes below.

Supplementary Note 1

An information processing system according to Supplementary Note 1 is an information processing system including: an authentication unit that performs biometric authentication by using biometric information about a first user; an acquisition unit that acquires information about an action history of the first user in the case where the biometric authentication is successful; an storage unit that stores the information about the action history; a generation unit that generates risk information indicating a risk related to the first user, on the basis of the stored information about the action history; and an output unit that outputs the risk information about the first user in response to a request of a second user who is different from the first user.

Supplementary Note 2

An information processing system according to Supplementary Note 2 is the information processing system according to Supplementary Note 1, wherein the output unit outputs the risk information about the first user in accordance with a result of a collation/verification process using biometric information.

Supplementary Note 3

An information processing system according to Supplementary Note 3 is the information processing system according to Supplementary Note 1 or 2, wherein the information about the action history includes at least one of a movement history of the first user, environmental information corresponding to the movement history, human body information, and a conversation history.

Supplementary Note 4

An information processing system according to Supplementary Note 4 is the information processing system according to any one of Supplementary Notes 1 to 3, further including a threshold change unit that changes a threshold of the biometric authentication such that the biometric authentication is hardly successful, in the case where an action pattern of the first user in a predetermined period does not match a past action pattern of the first user.

Supplementary Note 5

An information processing system according to Supplementary Note 5 is the information processing system according to any one of Supplementary Notes 1 to 4, wherein the authentication unit performs the biometric authentication, by using operation information acquired by detecting a gesture around a shielding object that partially covers a face of the first user, in addition to the biometric information about the first user.

Supplementary Note 6

An information processing system according to Supplementary Note 6 is the information processing system according to any one of Supplementary Notes 1 to 5, wherein the authentication unit performs the biometric authentication, by using shielding object change information acquired by detecting a change in a surface area or a position of a shielding object that partially covers a face of the first user, in addition to the biometric information about the first user.

Supplementary Note 7

An information processing system according to Supplementary Note 7 is the information processing system according to any one of Supplementary Notes 1 to 6, further including a factor determination unit that determines whether a factor of occurrence of false rejection in the biometric authentication is caused by an input condition of the biometric information, or by a change with time in the biometric information, on the basis of an authentication history of the biometric authentication.

Supplementary Note 8

An information processing system according to Supplementary Note 8 is the information processing system according to any one of Supplementary Notes 1 to 7, further including: a display unit that displays body temperature of the first user acquired as the information about the action history; and a display aspect change unit that changes a display aspect of the display unit, on the basis of the measured body temperature.

Supplementary Note 9

An information processing method according to Supplementary Note 9 is an information processing method executed by at least one computer, the information processing method including: performing biometric authentication by using biometric information about a first user; acquiring information about an action history of the first user in the case where the biometric authentication is successful; storing the information about the action history; generating risk information indicating a risk related to the first user, on the basis of the stored information about the action history; and outputting the risk information about the first user in response to a request of a second user who is different from the first user.

Supplementary Note 10

A recording medium according to Supplementary Note 10 is a recording medium on which a computer program that allows at least one computer to execute an information processing method is recorded, the information processing method including: performing biometric authentication by using biometric information about a first user; acquiring information about an action history of the first user in the case where the biometric authentication is successful; storing the information about the action history; generating risk information indicating a risk related to the first user, on the basis of the stored information about the action history; and outputting the risk information about the first user in response to a request of a second user who is different from the first user.

Supplementary Note 11

A computer program according to Supplementary Note 11 is a computer program that allows at least one computer to execute an information processing method, the information processing method including: performing biometric authentication by using biometric information about a first user; acquiring information about an action history of the first user in the case where the biometric authentication is successful; storing the information about the action history; generating risk information indicating a risk related to the first user, on the basis of the stored information about the action history; and outputting the risk information about the first user in response to a request of a second user who is different from the first user.

This disclosure is not limited to the examples described above and is allowed to be changed, if desired, without departing from the essence or spirit of this disclosure which can be read from the claims and the entire specification. An information processing system, an information processing method, and a recording medium with such changes are also intended to be within the technical scope of this disclosure.

DESCRIPTION OF REFERENCE CODES

10 Information processing system
11 Processor
14 Storage apparatus
18 Sensor
110 Biometric authentication unit
111 Operation information acquisition unit
112 Shielding object information acquisition unit
120 Action history acquisition unit
130 Action history storage unit
140 Risk information generation unit
150 Risk information output unit
151 Verification unit
200 Threshold change unit
210 Action pattern storage unit
220 Action pattern comparation unit
230 Threshold determination unit
300 Factor determination unit
310 Authentication history storage unit
320 Determination processing unit
330 Determination result output unit
410 Body temperature display unit
420 Display aspect change unit

What is claimed is:

1. An information processing system comprising:
at least one memory that is configured to store instructions; and
at least one processor that is configured to execute the instructions to:
perform biometric authentication by using biometric information about a first user and also by using operation information obtained by detecting a gesture around a shielding object that partially covers a face of the first user;
obtain information about an action history of the first user in the case where the biometric authentication is successful;
accumulate the information about the action history;
generate risk information indicating a risk related to the first user, on the basis of the accumulated information about the action history; and
output the risk information about the first user in response to a request of a second user who is different from the first user.

2. The information processing system according to claim 1, wherein the at least one processor is configured to execute the instructions to output the risk information about the first user in accordance with a result of a collation process using the biometric information.

3. The information processing system according to claim 1, wherein the information about the action history further includes at least one of human body information and a conversation history.

4. The information processing system according to claim 1, wherein the at least one processor is configured to execute the instructions to change a threshold of the biometric authentication such that the biometric authentication is hardly successful, in the case where an action pattern of the first user in a predetermined period does not match a past action pattern of the first user.

5. The information processing system according to claim 1, wherein the at least one processor is configured to execute the instructions to perform the biometric authentication, by using shielding object change information obtained by detecting a change in a surface area or a position of a shielding object that partially covers a face of the first user, in addition to the biometric information about the first user.

6. The information processing system according to claim 1, wherein the at least one processor is configured to execute the instructions to determine whether a factor of occurrence of false rejection in the biometric authentication is caused by an input condition of the biometric information, or by a change with time in the biometric information, on the basis of an authentication history of the biometric authentication.

7. The information processing system according to claim 1, wherein the at least one processor is configured to execute the instructions to:
display body temperature of the first user obtained as the information about the action history; and
change a display aspect of the display unit, on the basis of the measured body temperature.

8. An information processing method executed by at least one computer,
the information processing method comprising:
performing biometric authentication by using biometric information about a first user and also by using operation information obtained by detecting a gesture around a shielding object that partially covers a face of the first user;
obtaining information about an action history of the first user in the case where the biometric authentication is successful;
accumulating the information about the action history;
generating risk information indicating a risk related to the first user, on the basis of the accumulated information about the action history; and
outputting the risk information about the first user in response to a request of a second user who is different from the first user.

9. A non-transitory recording medium on which a computer program that allows at least one computer to execute an information processing method is recorded, the information processing method including:

performing biometric authentication by using biometric information about a first user, and also by using operation information obtained by detecting a gesture around a shielding object that partially covers a face of the first user;

obtaining information about an action history of the first user in the case where the biometric authentication is successful;

accumulating the information about the action history;

generating risk information indicating a risk related to the first user, on the basis of the accumulated information about the action history; and outputting the risk information about the first user in response to a request of a second user who is different from the first user.

* * * * *